United States Patent
Abuhasel et al.

(10) Patent No.: US 10,113,213 B2
(45) Date of Patent: Oct. 30, 2018

(54) PROCESSING AND APPLICATION OF A PURIFICATION SYSTEM FOR A NEW ALTERNATIVE SOURCE OF ENERGY

(71) Applicants: University of Bisha, Bisha (SA); Prince Sattam Bin Abdulaziz University, Alkharj (SA)

(72) Inventors: Khaled A. Abuhasel, Aseer (SA); Saleh Ali Alkahtani, Alkharj (SA)

(73) Assignees: University of Bisha, Bisha (SA); Prince Sattam Bin Abdulaziz University, Alkhari (SA)

( * ) Notice: Subject to any disclaimer, the term of this patent is extended or adjusted under 35 U.S.C. 154(b) by 64 days.

(21) Appl. No.: 15/264,016

(22) Filed: Sep. 13, 2016

(65) Prior Publication Data

US 2016/0376680 A1    Dec. 29, 2016

Related U.S. Application Data

(63) Continuation of application No. 14/303,312, filed on Jun. 12, 2014, now Pat. No. 9,446,973.

(51) Int. Cl.
| | |
|---|---|
| C22B 3/18 | (2006.01) |
| C22B 3/00 | (2006.01) |
| C22B 3/02 | (2006.01) |
| C22B 3/24 | (2006.01) |
| C02F 1/04 | (2006.01) |
| C02F 1/44 | (2006.01) |
| C02F 1/66 | (2006.01) |
| C02F 1/461 | (2006.01) |
| C02F 1/469 | (2006.01) |
| C02F 3/32 | (2006.01) |
| C02F 9/00 | (2006.01) |
| C12P 7/64 | (2006.01) |
| C12N 1/12 | (2006.01) |
| C02F 101/20 | (2006.01) |
| C02F 101/32 | (2006.01) |
| C02F 103/10 | (2006.01) |

(52) U.S. Cl.
CPC ............... *C22B 3/18* (2013.01); *C02F 1/041* (2013.01); *C02F 1/441* (2013.01); *C02F 1/4693* (2013.01); *C02F 3/322* (2013.01); *C02F 9/00* (2013.01); *C12N 1/12* (2013.01); *C12P 7/64* (2013.01); *C22B 3/02* (2013.01); *C22B 3/24* (2013.01); *C22B 11/04* (2013.01); *C02F 1/461* (2013.01); *C02F 1/66* (2013.01); *C02F 2101/20* (2013.01); *C02F 2101/32* (2013.01); *C02F 2103/10* (2013.01); *Y02P 10/234* (2015.11); *Y02W 10/37* (2015.05)

(58) Field of Classification Search
CPC .......... C02F 1/041; C02F 1/441; C02F 1/461; C02F 1/4693; C02F 1/66; C02F 2101/20; C02F 2101/32; C02F 2103/10; C02F 3/322; C02F 9/00; C12N 1/12; C12P 7/64; C22B 11/04; C22B 3/02; C22B 3/18; C22B 3/24; Y02P 10/02; Y02P 10/234; Y02W 10/37
See application file for complete search history.

(56) References Cited

U.S. PATENT DOCUMENTS

| | | | |
|---|---|---|---|
| 9,446,973 B2 * | 9/2016 | Abuhasel | ............... C02F 3/322 |
| 2006/0196836 A1 | 9/2006 | Arakel et al. | |
| 2011/0177550 A1 | 7/2011 | McMurran | |

* cited by examiner

*Primary Examiner* — Deborah K Ware
(74) *Attorney, Agent, or Firm* — Oblon, McClelland, Maier & Neustadt, L.L.P.

(57) ABSTRACT

The present disclosure describes a process for using saline water, and saline reject water produced in water purification, to use for gold mining production, and growing and harvesting algae. The disclosure also describes a method for growing and harvesting algae utilizing saline water as growth medium for recycling waste water to extract the remaining metals out of waste water. The harvested algae may be used in various applications including but not limited to water purification for gold mining production and to extract metals out of remaining waste water.

18 Claims, 1 Drawing Sheet

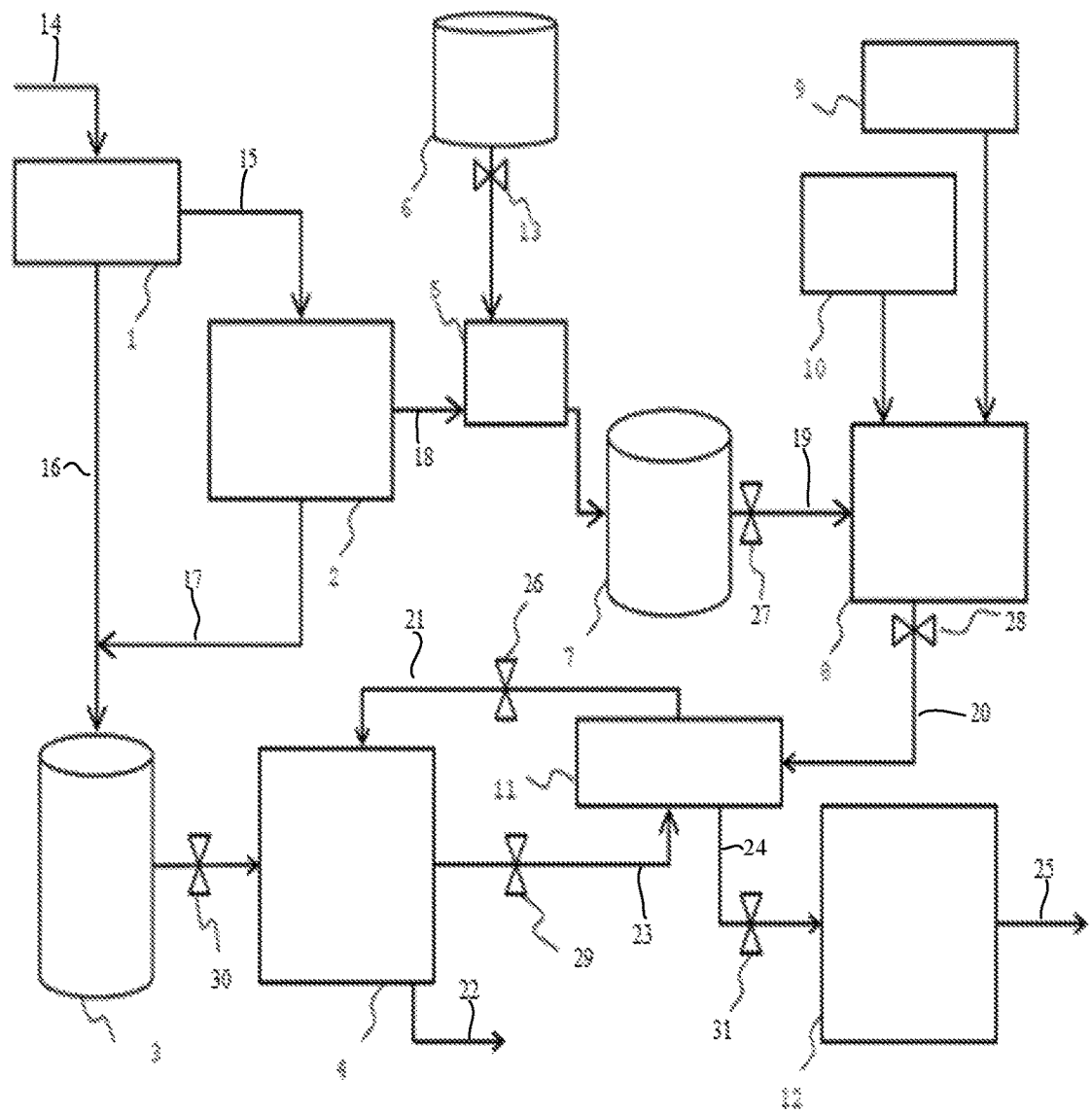

PROCESSING AND APPLICATION OF A PURIFICATION SYSTEM FOR A NEW ALTERNATIVE SOURCE OF ENERGY

This application is a continuation of application Ser. No. 14/303,312, filed Jun. 12, 2014, now U.S. Pat. No. 9,446,973, issued Sep. 20, 2016. The patent application identified above is incorporated herein by reference in its entirety.

BACKGROUND OF THE INVENTION

Technical Field

The present disclosure relates to a method for the concurrent production of algae and the separation of gold from a gold ore using an algal mat and a system for the production of algae and the separation of gold from a gold ore using an algal mat.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Algae thrive in turbid, brackish water environments with little more than basic nutrients and sunshine. They grow far more rapidly than conventional crops, and generate a much higher fraction of their biomass as oil (up to 60%, versus 2%-3% for soybeans).

As recently, algae have become significant organisms for biological purification of wastewater since they are able to accumulate plant nutrients, heavy metals, pesticides, organic and inorganic toxic substances and radioactive matters in their cells/bodies (Kalesh N S, Nair S M The Accumulation Levels of Heavy Metals (Ni, Cr, Sr, & Ag) in Marine Algae from Southwest Coast of India. Toxicological & Environmental Chemistry 2005; 87(2): 135-146; Jothinayagi N, Anbazhagan C. Heavy Metal Monitoring of Rameswaram Coast by Some Sargassum species. American-Eurasian Journal of Scientific Research 2009; 4 (2): 73-80; Alp M T, Sen B, Ozbay O. Heavy Metal Levels in Cladophora glomerata which Seasonally Occur in the Lake Hazar. Ekoloji, 20 (78): 13-17. doi: 10.5053/ekoloji.2011.783; Alp M T, Ozbay O, Sungur M. A. Determination of Heavy Metal Levels in Sediment and Macroalgae (*Ulva* sp. and *Enteromorpha* sp.) on the Mersin Coast 2011. Ekoloji 21, 82, 47-55 (2012)—each incorporated herein by reference in its entirety). These specific features have made algal wastewater treatment systems a significant low-cost alternative to complex expensive treatment systems particularly for purification of municipal wastewaters.

In addition, algae harvested from treatment ponds are widely used as nitrogen and phophorus supplements for agricultural purpose and can be subjected to fermentation in order to obtain energy from methane. Algae are also able to accumulate highly toxic substances such as selenium, zinc and arsenic in their cells and/or bodies thus eliminating such substances from aquatic environments. Radiation is also an important type of pollution as some water contains naturally radioactive materials, and others become radioactive through contamination. Many algae can take up and accumulate many radioactive minerals in their cells even from greater concentrations in the water (Palmer, C. M. A composite rating of algae tolerating organic pollution. J. Phycology. 1969; 5: 78-82—incorporated herein by reference in its entirety). MacKenthun emphasized that Spirogyra can accumulate radio-phosphorus by a factor 850,000 times that of water (MacKenthun, K. M. Radioactive wastes. Chapt 8. In The Practice of Water Pollution Biology. U.S. Dept. Interior, Fed. Water Pol. Contr. Admin., Div. of Tech. Support.U.S. Printing Office 1969—incorporated herein by reference in its entirety).

It is well known that algae have an important role in self-purification of organic pollution in natural waters (Sen, B. ve Nacar, V. Su Kirliliği ve Algler. Firat Havzasi I. Cevre Sempozyumu Bildiriler Kitabi. 1988; 405-21—incorporated herein by reference in its entirety). Moreover, many studies revealed that algae remove nutrients especially nitrogen and phosphorus, heavy metals, pesticides, organic and inorganic toxins, pathogens from surrounding water by accumulating and/or using them in their cells (Reddy, K. R. Fate of Nitrogen and Phosphorus in a Wastewater Retention Reservoir Containing Aquatic Macrophytes. Journal of Environmental Quality, 1983; 12(1):137-41; Lloyd, B. J. and Frederick, G. L. Parasite removal by waste stabilisation pond systems and the relationship between concentrations in sewage and prevalence in the community, Water Science and Technology 2000; 42(10):375-86—each incorporated herein by reference in its entirety). Also, studies showed that algae may be used successfully for wastewater treatment as a result of their bioaccumulation abilities (Oswald, W. J. The role of microalgae in liquid waste treatment and reclamation. In: C. A. Lembi and J. R. Waalnd (eds). Algae and Human Affairs, Cambridge University Press 1988a; 403-31—incorporated herein by reference in its entirety).

Wastewater treatment systems which are applied to improve or upgrade the quality of a wastewater involves physical, chemical and biological processes in primary, secondary or tertiary stages. Primary treatment removes materials that will either float or readily settle out by gravity. It includes the physical processes of screening, contamination, grit removal, and sedimentation. While the secondary treatment is usually accomplished by biological processes and removes the soluble organic matter and suspended solids left from primary treatment. Tertiary or advanced treatment is process for purification in which nitrates and phosphates, as well as fine particles are removed (Droste, R. L. Theory and Practice of water and wastewater treatment, John Wiley and Sons, New York 1997—incorporated herein by reference in its entirety). However initial cost as well as operating cost of wastewater treatment plant including primary, secondary or advanced stages is highly expensive (Oswald,W. J. Ponds in twenty first century. Water Science and Technology 1995; 31(12):1-8—incorporated herein by reference in its entirety).

Some algae produce lipids that can be converted to biodiesel or green diesel. Some strains produce ethanol. Algae biomass is also used as food, animal feed and fertiliser, but it isn't reasonable to expect 100% substitution—there are too many complications. In 20 years fuel substitution is expected to be in the 5%-8% range.

Creating biofuels from microbes has many advantages. Algae can grow in low lying areas unsuitable for conventional crops. Algae can yield 8,000 litres of fuel per acre per year, compared with 2,600 litres for palm oil and 200 litres for soy. Algae can use brackish water or wastewater as a growing medium, eliminating the freshwater needs of ethanol production. Algae production does not compete with food crops such as corn or soy for acreage, nutrients or fresh water. Furthermore, biofuels are similar enough to gasoline and diesel that they do not require special treatment during transportation and mixing at the refinery.

Recent studies conclude that this algae dewatering process costs over $3,000 in energy alone to produce one ton of dry weight biomass equivalent, making algae an uneconomic source of fuel when compared to fossil fuels. Nevertheless, a comprehensive industry survey undertaken by the Algal Biomass Organization last year found that more than 35% of industry participants believe it is either very likely or extremely likely that algae-based fuels will be cost-competitive with fossil fuels by 2020.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the disclosure describes a process for gold mining and algae production.

In another embodiment the process comprises treating a salt water stream having a first salt concentration, wherein the treating is carried out with at least one of electrodialysis reversal, reverse osmosis or mechanical vapor compression in a first water purification system to form: (i) a first purified water stream having a second salt concentration lower than the first salt concentration, and (ii) a first saline water stream having a third salt concentration higher tha the first salt concentration.

In another embodiment the process comprises treating a gold ore with the first purified water stream to separate gold from the gold ore and to form a first waste water.

In another embodiment the process comprises treating the waste water comprising metal ions in a waste water processing unit comprising an algae mat to form (i) a third purified water stream and (ii) the algae mat bound to the metal ions, and further treating the gold ore with the third purified water stream.

In another embodiment the process comprises feeding the first saline water stream to a bioreactor containing algae to form a first biomass in the saline water of the first saline water stream and to form a first saline biomass stream.

In another embodiment the process comprises feeding the first saline biomass stream to an algae growth and harvesting chamber to grow the algae and to form a concentrated biomass.

In another embodiment the process comprises feeding the concentrated biomass to the waste water processing unit and forming a filter in the form of an algae mat from the biomass in the waste water processing unit.

In another embodiment the process comprises removing the algae mat from the waste water processing unit and isolating gold and oil from the algae mat.

In another embodiment the disclosure describes a system for gold mining and algae production.

In another embodiment the system comprises a first water purification system that treats a salt water stream having a first salt concentration and forms a first purified water stream having a second salt concentration lower than the first concentration and a first saline water stream having a third salt concentration higher than the first concentration.

In another embodiment the system comprises a gold mining production system that treats a gold ore with the first purified water stream to separate gold from the gold ore and to form a first waste water.

In another embodiment the system comprises a waste water processing unit comprising an algal mat that treats the waste water comprising metal ions to form a second purified water stream and the algae mat bound to the metal ions wherein the waste water processing unit further treats the gold ore with the second purified water stream and/or an algal mat formed by producing algae in a waste water stream.

In another embodiment the system comprises a bioreactor containing algae that forms a first biomass in the saline water of the first saline water stream and forms a first saline biomass stream wherein the first saline water stream is fed to the bioreactor containing algae.

In another embodiment the system comprises an algae growth and harvesting chamber that grows the algae to form a concentrated biomass by feeding the first saline biomass stream to the algae growth and harvesting chamber wherein the concentrated biomass is fed to the waste water processing unit and forms a filter in the form of an algae mat from the biomass in the waste water processing unit.

In another embodiment the system isolates gold and oil from the algae mat.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 illustrates a flow diagram for using salt water for gold mining production.

DETAILED DESCRIPTION OF THE EMBODIMENTS

Referring now to the drawings, wherein like reference numerals designate identical or corresponding parts throughout the several views.

The economic and environmental incentive to reduce the energy costs associated with algae processing is driving increased levels of industry research, particularly on ways to reduce the cost of algae dewatering. Pall Corporation, for example, has developed the algae separation and concentration filter (ASCF) that uses a hollow-fiber filter technology for chemical cleaning to remove organic and inorganic debris.

One of the common associations with gold in detrital deposits is the association of gold with uranium and carbon. This holds true in the Witwatersrand and all the other gold deposits of a detrital nature. For many years the origin of the carbon was hotly debated with the most recent evidence holding that it is from primitive life forms that lived in the distant past in the Archean.

Algae exposed at the intertidal zone similar to the ancient algae that trapped gold. Even today this kind of mat could be a good place to search for gold. It has been posited that these algae formed stromatolite-type structures that acted as a trap for gold and uranium minerals.

Many gold bearing deposits are located at the bottom of a ancient stream channel. The gold was deposited by dropping from suspension to form stringers of gold. These stringers of gold are common in detrital gold deposits. Sometimes there is a layer of carbon that is as thin as a pencil line that is so rich in gold and other minerals that they are mineable. In many detrital deposits the slim lines occur at a regular frequency to the extent that the entire deposit is mined so that it can undergo further ore dressing to free the gold so it can undergo even further treatment usually by being leached with a solution of cyanide.

The inland brackish water that constitute the feed for water purification plants has a higher quality (i.e. lower salinity) compared to seawater and is more suitable for water purification. Depending on level of salinity and cost, various methods are utilized for purifying the brackish water, such as reverse osmosis (RO), electro-dialysis reversal (EDR), or similar membrane techniques. Water purification process of brackish water produces purified water and saline reject water as main product and by-product, respectively. The produced saline reject water usually contains a higher concentration of various salts in water compared to the brackish water. A number of subsequent purifications may be performed to extract the remaining purified water from the saline reject water. However, the salinity of the saline reject water increases after each subsequent purification, leading to increased cost, and complexity of the water purification procedure. Therefore, after a number of purification steps, the saline reject water becomes highly saline.

The highly saline reject water is considered as waste in the purification process and therefore is disposed. However, disposing such highly saline reject water is complicated and costly. Because of the costs and problems associated with the disposal of the highly saline reject water, there exists a need for developing methods for minimizing such undesirable liquid by-products, or recycling and/or transforming the waste into a valuable product. Moreover, extracting gold by using fresh water is expensive.

In one embodiment the disclosure describes a method for using highly saline water and/or a water stream obtained by treating saline water with an algae growth system, as an alternative to disposal, to produce a variety of valuable products such as gold mining production, and growing algae to extract metals. In addition the method also recycles the waste water for the production of gold mining.

According to one embodiment, FIG. 1 depicts a process flow diagram for using brackish/saline water for gold mining production. First, a stream of water 14 having a salinity content of 0.05% salinity or greater is supplied to a first water purification system 1. The stream of water 14 may be brackish water, saline water, or any combination thereof. A stream having a combination of brackish water and saline water may have a brackish and saline percent composition including but not limited to 50% brackish water and 50% saline water, 20% brackish water and 80% saline water, 80% brackish water and 20% saline water, 30% brackish water and 70% saline water, 70% brackish water and 30% saline water, 100% brackish water, or 100% saline water. The brackish water has a salinity in the range of 0.5-30 grains of salt per liter, 5-20 grams of salt per liter, or 10-15 grams of salt per liter. The saline water has a salinity in the range of 30-50 grams or salt per liter, 32-48 grams of salt per liter, or 35-45 grams of salt per liter. The brackish water and/or the saline water may be supplied from water resources including but not limited to river water, lake water, ocean water and/or another water purification syst e.g., reverse osmosis or distillative desalinization. The brackish water and/or the saline water may also comprise magnesium (Mg) and sulphate ($SO_4$) ions in dissolved form.

The first water purification system 1 removes suspended solids and/or gases from the brackish water 14 and produces a first stream of purified water 16 and a first stream of saline reject water 15. The water purification system reduces the concentration of salt in the water stream so that the purified water 16 has a lower concentration of salt than the stream of water 14 and so that the stream of saline reject water 15 has a higher concentration of salt than the stream of water 14. The purified water 16 produced by the first water purification system may have various purity levels to provide water for human consumption, animal consumption or agricultural purposes. The purified water 16 is stored in a purified water reservoir 3.

The stream of saline reject water 15 is supplied to a second water purification system 2 that further processes the saline reject water to produce a stream of highly saline reject water 18 and a second stream of purified water 17. The stream of highly reject saline water 18 has a higher concentration of salt than the stream of saline reject water 15. The second stream of purified water 17 has a lower salt concentration than the stream of saline reject water 15. The first stream of purified water 16 and the second stream of purified water 17 are both stored in a purified water reservoir 3. The purified water by the first stream of purified water 16 and the second stream of purified water 17 may also be gathered in a plurality of water reservoirs.

In one embodiment the water purification system 1 and the water purification system 2 are of the same configuration. The water purification system 1 and the water purification system 2 comprise an intake chamber; an osmotic chamber coupled to the intake chamber; at least one ammonia stripping column coupled to the osmotic chamber; at least one ion exchange coupled to the at least one ammonia stripping column; a breakpoint chlorination chamber coupled to the at least one ion exchange column; and an output from the breakpoint chlorination chamber.

In another embodiment the stream of brackish/saline water 14 enters an intake chamber of the water purification system 1 or the stream of saline reject water 15 enters the water purification system 2. The intake chamber directs the seawater from the intake chamber into an osmotic chamber, allowing osmosis of water molecules through a membrane located between the seawater and a concentrated ammonia solution in the osmotic chamber. In the osmotic chamber the concentrated ammonia solution is converted to a diluted solution through osmosis. The pH of the diluted solution is adjusted to a pH of 11 or higher. Ammonia is removed from the diluted solution using multistage air-stripping columns which adjusts the pH of the diluted solution to approximately neutral after the air-stripping. Then the ammonia is removed from the diluted solution using at least one ion-exchange column after the air-stripping and the ammonia is removed from the diluted solution using breakpoint chlorination after ion exchange. Breakpoint chlorination includes adding a solution of chlorine to the water so that the ammonia may be oxidized and removed and only free chlorine remains.

In another embodiment osmosis occurs between seawater and a second solution, resulting in a diluted solution. The ammonia is stripped from the diluted solution at an elevated pH level, and ammonia is removed from the diluted solution using ion exchange. Breakpoint chlorination is then performed on the diluted solution to effectively remove any remaining ammonia.

The water purification systems 1 and 2 convert water having a salinity content of 0.05% or higher to purified water by undergoing osmosis with a concentrated ammonia solution, removing ammonia from the solution (ammonia concentration of 500 mg/L or less) using air-stripping columns at an elevated pH, removing ammonia from the solution using ion-exchange methods, and a breakpoint chlorination step to remove any remaining ammonia in the solution.

In another embodiment the water purification system 1 and the water purification system may include a plurality of chambers for different processing stages. The first chamber may be a seawater intake chamber, which may be equipped with a microstrainer, typically for removal of objects measuring at least 5 microns. In another embodiment the algae may be used as a microstrainer. The intake chamber may be connected to an osmotic chamber. The osmotic chamber may have an osmotic membrane with a seawater tank on one side and an ammonia tank, containing a concentrated ammonia solution, on the other side. The seawater may enter the seawater tank from the intake chamber, and using the osmotic membrane, water molecules may migrate into the ammonia tank to a solution that may typically contain approximately molar ammonia as a solute. The concentration of ammonia in the ammonia tank may be greatly diluted, e.g. 5 times, through the osmotic process. The pH of the diluted solution may then be adjusted to 11 or higher, typically using sodium hydroxide.

The solution may then be introduced to multistage air-stripping columns to remove ammonia, typically to a concentration of 500 mg/L or less. The column packing material may be specially designed to achieve ammonia removal efficiency of 85% or better when using air for the stripping operation. The gas stream coming out of the ammonia stripping columns may be a mixture of ammonia, oxygen, nitrogen, and water vapor. This gas stream may then be passed through condensation tube, which may typically be a series of longitudinal conduits designed to condense the ammonia and the moisture content in the gas stream, allowing oxygen, nitrogen, and a low concentration of ammonia to escape. Subsequently, the escaped (post-condensation) gas stream may be directed to a heating chamber, and the heated gas may then be recirculated back to the ammonia stripping columns. The condensate, containing water and ammonia, may then be recirculated back to the ammonia solution in the osmotic chamber.

The pH of the water after ammonia stripping may then be adjusted to almost neutral (typically 6.5 to 7.5), using an acid including but not limited to sulfuric acid. The water may then be passed through a plurality of ion exchange columns for ammonia removal which decreases the ammonia concentration in the water to less than 5 mg/L. The ion exchange resin is regenerated using an acid including but not limited to concentrated sulfuric acid. This solution can be recirculated until the solution is almost saturated with ammonium sulfate, and it may then be discharged through a recirculating fluid output. Concentrated sodium hydroxide solution may be used to adjust the pH of the solution to above 11, and ammonia gas may eventually be removed by air stripping columns. The gas from the air stripping columns may be directed to the condensation tube. The spent solution may contain high concentrations of sodium ion, sulfate, and some residual ammonia, and the solution can be diluted with seawater before discharging back to the ocean.

The water may then undergo breakpoint chlorination, typically in a chamber, in which the remaining ammonia in the water may be oxidized to nitrogen gas and chloramines using chlorine gas or hypochlorites. The resulting water product may typically contain total dissolved solids of 150 mg/L or less with a free chlorine level in the range of 0.2 mg/L to 1 mg/L.

The ammonia concentration of the solution exiting the osmotic chamber may be in the range of 30,000 mg/L even after 5-time dilution through the osmotic process. The physical process of condensation may be used to separate most of the air from the ammonia. The ammonia condensate may be completely recirculated to the ammonia solution in the osmotic chamber, and the escaped air stream may be recirculated to the air stripping columns. A heat-exchange system may be used to extract heat from the condensation process. The extracted heat may be used to heat the recirculated air stream.

The mixture of air and ammonia is discharged into the atmosphere or treated with the biological processes of nitrification-denitrification.

In one embodiment the water purification system 1 and the water purification system 2 may provide a completely closed system without releasing any ammonia to the atmosphere.

In another embodiment the water purification system 1 and the water purification system 2 treat the stream of saline water by a method of electrodialysis. NaCl separated during electrodialysis may be subjected to electrolysis to form NaOH. The NaOH may be reacted with ammonia and $CO_2$ to form soda ash. $MgOH_2$ may also be precipitated and reacted with the additive $CO_2$ to precipitate $MgCO_3$. $MgCO_3$ is then discarded through an extract remaining metals unit 12.

The purified water reservoir 3 supplies the purified water to a gold mining production system 4. The gold mining production system 4 comprises a gold ore. The gold ore comprises gold and other materials including but not limited to silver, mercury, copper, sulfide, calaverite, sylvanite, nagyagite, petzite, and krennerite. The gold mining production system separates a gold compound 22 from the gold ore. Preferably the gold compound has a purity of gold of 50% or greater. More preferably the gold compound 22 is at least 90% pure gold.

The stream of highly saline reject water 18 has a salinity in the ange of 0-500 grams of salt per liter, 100-400 grams of salt per liter, or 150-350 grams of salt per liter.

The first water purification system 1 and the second water purification system 2 may have systems including but not limited to reverse osmosis, electro-dialysis reversal, and mechanical vapor compression distillation.

In another embodiment the highly saline reject water 18 may be treated in a treatment unit 5. The treatments in the optional treatment unit 5 include but are not limited to treatment with a UV lamp, heating, or addition of materials to change chemical or physical properties. An additive chamber 6 includes additives to be added to the treatment unit 5. In one embodiment the additive chamber 6 comprises one container of additives. In another embodiment the additive chamber 6 has a plurality of separate containers for storing materials to be added to the treatment unit 5. The additive chamber 6 may include one separate container or a plurality of separate containers for storing the materials to be added to the optional treatment unit 5. The additive chamber 6 lies adjacent to the optional treatment unit 5.

Carbon dioxide, as $CO_2$ gas may be supplied from an industrial source as an additive in the additive chamber 6 and injected into the highly reject saline water 18 in the treatment unit 5 to provide a desirable level of $CO_2$ in the water for subsequent use in algae growth and/or harvesting in the algae growth and harvesting chamber 8. The $CO_2$ may be derived through drilling processes during mining operations or other sources.

Municipal waste water may also be used as an additive in the additive chamber 6. Part of the treated waste having low salinity may be fed for use in saline tolerant plant farming or algae growth in the algae growth and harvesting chamber 8.

In another embodiment the containers comprising the additive chamber 6 may have a. separate control valve 13 for each container in the additive chamber 6. The control valve 13 controls the flow rate of addition of additives in the additive chamber 6 to the treatment unit 5. The flow rate may be reduced or increased by the control valve 13 if more or less additives need to be introduced to the treatment unit 5. After passing through the treatment unit 5 the highly saline reject water 18 is sent to a bioreactor containing microalgae 7.

Once the water having adjusted salinity 18 is at a desired salinity level, $CO_2$ level, pH level, and nutrient level, it may be fed to a plurality of bioreactors 7. The bioreactors 7 may take the form of including but not limited to ponds, preferably covered ponds. The bioreactors 7 may include a combination of a bioreactor and a subsequent pond in combination. Each of the bioreactors 7 houses microalgae, which may be the same or different. Multiple streams of different water salinity are provided for optimum production of algae in each case. The bioreactor 7 may be a batch, a fed batch, or a continuous bioreactor. Preferably the bioreactor 7 is a fed batch bioreactor.

The stream of highly reject saline water 18 is treated in the treatment unit 5 to provide the proper pH levels and have sufficient levels of $CO_2$. This may enable some species preferred for ethanol production and some species for bio-diesel production to be harvested. The *Botryococcus* species is suitable for ethanol production but has a longer growth time which requires a separated flow from other species selected for biodiesel feedstock. The biodiesel species, in particular *Chloralla* and *Spirulina* have a short growth time. Each of the bioreactors 7 comprises an algae which may be of the same or different species. Multiple streams of different water salinity from the treatment unit 5 are provided separately or at the same time to each bioreactor 7 in order to provide the preferred growth rate of the algae. Algae species that are grown in the bioreactor include but are not limited to *Acaryochloris, Amphora, Anabaena, Anacystis, Anikstrodesmis, Botryococcus, Chaetoceros, Chlorella, Chlorococcum, Crocosphaera, Cyanotheca, Cyclotella, Cylindrotheca, Dunaliella, Euglena, Hematococcus, Isochrysis, Lyngbya, Microcystis, Monochrysis, Monoraphidium, Nannochloris, Nannochloropsis, Navicula, Nephrochloris, Nephroselmis, Nitzschia, Nodularia, Nostoc, Oochromonas, Oocystis, Oscillartoria, Pavlova, Phaeodactylum, Platymonas, Pleurochrysis, Porhyra, Prochlorococcus, Pseudoanabaena, Pyramimonas, Selenastrum, Stichococcus, Synechococcus, Synchocystis, Thalassiosira, Thermosynechocystis,* and *Trichodesmium* species. Residence time of the algae in the bioreactors 7 is in the range of 4-14 days, 6-13 days, and 7-10 days. Preferably residence time of the algae in the bioreactors 7 is in the range of 7-10 days.

In another embodiment the highly reject saline water 18 passes directly from the water purification system 2 to the bioreactor containing microalgae 7 and does not pass through a treatment unit.

The bioreactor containing microalgae 7 uses the highly reject saline water 18 to produce a stream of biomass 19 that enters an algae growth and harvesting chamber 8.

In the algae growth and harvesting chamber 8, a concentrated biomass 20 is grown and harvested. Preferably the biomass is algae. The biomass is grown, cultivated and/or harvested by providing the factors that influence the occurrence, growth, and production yield of algae or biomass. Factors that influence the occurrence, growth, and production yield of algae or biomass include carbon dioxide gas from a carbon dioxide source 10 and light from a light source 9. The carbon dioxide source 10 is preferably from industrial exhausts that produce high amounts of carbon dioxide to reduce the adverse environmental effects or the green house effect of carbon dioxide. The light source 9 may be from solar energy or from a UV lamp. Temperature favoring algae or biomass growth is also regulated. The temperature is in the range of 10-80° C., 12-40° C., or 1.6-27° C. Preferably the temperature side the algae growth and harvesting chamber 8 is in the range of 16-27° C.

The algae growth and harvesting chamber 8 produces the stream of concentrated biomass 20. The flow rate of the stream of concentrated biomass may be controlled by a control valve 28. The control valve 28 controls the flow rate of addition of the stream of concentrated biomass 20 to a waste water processing unit 11. The flow rate may be reduced or increased by the control valve 28 if more or less of the stream of concentrated biomass 20 needs to be added to the waste water processing unit 11.

The stream of concentrated biomass 20 is delivered to the waste water processing unit 11. The stream of concentration biomass 20 has a higher algae concentration than the stream of biomass that entered the algae growth and harvesting chamber 8. The waste water processing unit separates a stream of purified water 21 from a stream of water comprising heavy metals 4 using an algal mat that is formed from the stream of concentrated biomass 20. The algal mat comprises a plurality of layers of algae. The algal mat may have at least 10 layers of algae and may comprise a plurality of algal species.

In one embodiment the algal mat acts as a filter in the waste water processing unit 11 to create a stream of purified water 21 and to discard the metal ions from the waste water 23 to an extract remaining metals unit 12. A control valve 31 controls the flow rate of addition of the stream of water comprising heavy metals 24 to the extract remaining metals unit 12. The flow rate may be reduced or increased by the control valve 31 if more or less of the stream of water comprising heavy metals 24 needs to be added to the extract remaining metals unit 12. A group of metals 25 that is produced from the extract remaining metals unit 12 is the metal that is removed out of the algal biomass and from a gold ore from the gold mining production system 4.

The algal mat also comprises oil which can be used to produce biodiesel and bioethanol after extraction. Preferably the algal mat comprises 50% oil and carbohydrates.

In another embodiment the algal mat acts as a filter in the gold mining production system 4 to separate a gold product 22 from waste and other metals. In the gold mining production system 4 the gold from the gold ore contacts the algal mat and attaches to the algal mat. Preferably all other materials in the gold ore pass through the algal mat, leaving the gold product 22 attached to the algal mat.

The remaining waste water which has heavy metals is delivered to the waste water processing unit 11. The waste water processing unit 11 removes suspended metals from the stream of concentrated biomass 20 through algal biomass as a filter and purified water 21 that is delivered to the gold mining production system 4. The flow rate of the stream of purified water 21 may be controlled by a control valve 26. The control valve 26 controls the flow rate of addition of the stream of purified water 21 to the gold mining production system 4. The flow rate may be reduced or increased by the control valve 26 if more or less of the stream of purified water 21 needs to be added to the gold mining production system 4.

The gold mining production system separates gold from a gold ore by a method including but not limited to gold cyanidation, CIL circuit process, thiosulfate leaching, or a bulk leach extractable gold process. The gold mining production system 4 uses the stream of purified water 21 and the purified water from the purified water reservoir 3 to separate other metal ions in the gold ore from the gold.

In another embodiment the gold mining production system uses the method of CIL circuit process to separate the gold product 22 from the gold ore. Activated carbon is a highly porous material with distinct adsorptive properties. Gold complexes with either chloride or cyanide are strongly adsorbed by activated carbon. Gold recovery from solution by granular, begins by loading, or adsorbing the gold onto the activated carbon, which is accomplished in the carbon-in-leach (CIL) circuit. The CIL activated carbon system involves adding the carbon to the ore slurry in leaching tanks. The carbon adsorbs the gold from the solution as cyanidation of the ore proceeds.

In another embodiment the gold mining production system 4 uses the algal mat produced from the stream of concentrated biomass 20 to separate the gold product 22 from the gold ore. In one embodiment the algal mat is present in a sluice-type arrangement to separate the gold product 22 from the gold ore. The sluice box comprises riffles that may be coated with algae or algal biomass to capture gold particles as they pass through the sluice-type arrangement. In another embodiment the algal mat comprises a plurality of algal layers in the range of 1-10,000 layers of algae. Preferably the algal mat comprises 10-200 layers of algae. In another embodiment the algal mat may reduce the concentrations of potentially deleterious elements or metals including but not limited to aluminum, iron, manganese, nickel, zinc, and copper from the gold ore by 5- and 10-fold. The algal mat may separate the metals or elements from the gold ore by passing the gold ore through the algal mat. The metals then adhere to individual filaments of the algal mat. The structure of the biomass formed may act as carpeting grown on the riffles in the sluice-type arrangement. The algal mat comprises carbohydrates and proteins from the algae including but not limited to sulfate groups, carboxylate, and sulfhydryl. The positively charged heavy metals including gold from the gold ore bond to the negatively charged ions in the algal mat and the remaining materials from the gold ore pass through the algal mat without bonding to the algal mat. The remaining materials from the gold ore pass to the extract remaining metals unit 12.

In another embodiment an individual layer of the algal mat has a length in the range of 50-500 cm, 75-250 cm, or 90-150 cm. The algal mat has a width in the range of 50-500 cm, 75-250 cm, or 90-150 cm. Preferably the individual layer of the algal mat has a length in the range of 95-125 cm and a width in the range of 95-125 cm. An individual layer of the algal mat has a depth in the range of 0.5-50 cm, 1.0-45 cm, or 5-40 cm. Preferably the individual layer of the algal mat has a depth in the range of 1.0-10 cm.

The gold mining production system 4 separates a stream of waste water 23 comprising the metal ions from a gold product 22. The gold product 22 then exits the gold mining production system 4. The stream of waste water 23 is delivered to the waste water processing unit 11. The flow rate of the stream of waste water 23 may be controlled by a control valve 29. The control valve 29 controls the flow rate of addition of the stream of waste water 23 to the waste water processing unit 11. The flow rate may be reduced or increased by the control valve 29 if more or less of the stream of waste water 23 needs to be added to the waste water processing unit 11. In one embodiment metal ions are separated from the gold in the gold ore in the gold mining production system 4. The metal ions are separated from the gold in the gold ore by an algal mat. The algal mat traps the metal ions and isolates the metal ions. The gold passes through the algal mat to produce a gold product 22. After the algal mat isolates the metals ions, the metal ions are sent to the extract remaining metals unit 12. A stream of metals 25 is produced from the extract remaining metals unit 25.

Algae are modest microbes with amazing potential. They thrive in turbid, brackish water environments with little more than basic nutrients and sunshine. They grow far more rapidly than conventional crops, and generate a much higher fraction of their biomass as oil (up to 60%, versus 2%-3% for soybeans).

In one embodiment the disclosure describes a process for using saline water, and saline reject water produced in water purification, to use for gold mining production, and growing and harvesting algae. Also, the system describes an improved method for growing and harvesting algae with the use of saline water as growth medium for recycling waste water in order to extract the remaining metals out of waste water. Furthermore, the harvested algae may be used in various types and different categories of applications including but not limited to water purification systems for gold mining production, and extract metals out of remaining waste water.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A method of producing at least one metal from a gold ore and oil and/or ethanol from algae, the method comprising:
    (a) treating a first salt water stream having a first salt concentration X,
    wherein the treating is carried out with at least one of electrodialysis reversal, reverse osmosis, and mechanical vapor compression in a first water purification system to form: (i) a first purified water stream having a second salt concentration Y lower than X, and (ii) a first saline water stream having a third salt concentration Z higher than X,
    (b) treating the gold ore with the first purified water stream to separate gold from the gold ore and form a waste water comprising metal ions in a gold mining production system,
    (c) treating the first saline water stream in a second water purification system connected to the first water purification system to form a second saline water stream and a second purified water stream,
    wherein the second purified water stream has a fourth salt concentration A lower than Z, and the second saline water stream has a fifth salt concentration B higher than Z,
    (d) feeding the second saline water stream to a bioreactor containing algae to form a first algae biomass in the saline water of the second saline water stream,
    (e) feeding the first algae biomass to an algae growth and harvesting chamber to grow the first algae biomass and form a concentrated algae biomass, (f) feeding the concentrated algae biomass to a waste water processing unit,
wherein the concentrated algae biomass forms a first algae mat in the waste water processing unit, wherein the first algae mat comprises 10-200 layers of algae and each layer of algae has a length and/or a width of 50-500 cm and a depth of 0.5-50 cm,
(g) feeding the waste water comprising the metal ions from the gold mining production system to the waste water processing unit,
wherein the first algae mat in the waste water processing unit filters the waste water to form (i) a third purified water stream and (ii) the first algae mat bound to the metal ions,
(h) removing the first algae mat bound to the metal ions from the waste water processing unit,
(i) extracting the metal ions bound to the first algae mat to produce the at least one metal, and
(j) extracting oil and/or ethanol from the first algae mat.

2. The method of claim 1, wherein (g) further comprises feeding the third purified water stream to the gold mining production system for treating the gold ore.

3. The method of claim 1, wherein the first algae mat is formed from the concentrated algae biomass of the *Botryococcus* species, the *Chloralla* species, and the *Spirulina* species.

4. The method of claim 1, wherein the metal ions comprise at least one metal ion selected from the group consisting of a gold ion, a silver ion, a mercury ion, a copper ion, a lead ion, a tellurium ion, an antimony ion, an aluminum ion, an iron ion, a manganese ion, a nickel ion, a zinc ion, and a uranium ion.

5. The method of claim 1, wherein the gold ore further comprises uranium and the method further comprises feeding the concentrated algae biomass from the algae growth and harvesting chamber to the gold mining production system to form a second algae mat in the gold mining production system,
wherein the second algae mat contacts the gold ore and is configured to capture the uranium from the gold ore.

6. The method of claim 5, wherein the second algae mat has a stromatolite-type structure.

7. The method of claim 5, wherein the second algae mat is formed from the concentrated algae biomass of the *Botryococcus* species, the *Chloralla* species, and the *Spirulina* species.

8. The method of claim 5, wherein the second algae mat comprises 10-200 layers of algae and each layer of algae has a length and/or a width of 50-500 cm and a depth of 0.5-50 cm.

9. The method of claim 1, further comprising:
feeding the concentrated algae biomass from the algae growth and harvesting chamber to the gold mining production system to form a second algae mat in the gold mining production system,
wherein the second algae mat contacts the gold ore and binds the metal ions in the waste water to form the second algae mat bound to the metal ions while allowing passage of the gold separated from the gold ore through the second algae mat,
removing the second algae mat bound to the metal ions from the gold mining production system, and
extracting the metal ions bound to the second algae mat to produce the at least one metal.

10. The method of claim 9, wherein the second algae mat is formed from the concentrated algae biomass of the *Botryococcus* species, the *Chloralla* species, and the *Spirulina* species.

11. The method of claim 9, wherein the second algae mat comprises 10-200 layers of algae and each layer of algae has a length and/or a width of 50-500 cm and a depth of 0.5-50 cm.

12. The method of claim 9, wherein the metal ions comprise at least one metal ion selected from the group consisting of a gold ion, a silver ion, a mercury ion, a copper ion, a lead ion, a tellurium ion, an antimony ion, an aluminum ion, an iron ion, a manganese ion, a nickel ion, a zinc ion, and a uranium ion.

13. The method of claim 9, further comprising extracting oil and/or ethanol from the second algae mat.

14. The method of claim 1, further comprising:
feeding the first and/or the second purified water stream to a purified water reservoir to store purified water from the first and/or the second purified water stream,
wherein the purified water reservoir is connected to the first and/or the second water purification system and the gold mining production system; and
supplying the gold mining production system with the purified water from the purified water reservoir.

15. The method of claim 1, further comprising:
treating the second saline water stream with an additive in a treatment unit before feeding the second saline water stream to the bioreactor containing the algae,
wherein the additive is at least one selected from the group consisting of $CO_2$ gas, acids, and bases.

16. The method of claim 1, further comprising:
supplying to the algae growth and harvesting chamber at least one selected from the group consisting of carbon dioxide, UV light, and solar light.

17. The method of claim 15, wherein the first algae mat is formed from the concentrated algae biomass of a *Botryococcus* species, wherein the second saline water is treated with suitable levels of $CO_2$ and at least one of an acid and a base to grow the *Botryococcus* species in the bioreactor, and wherein ethanol is extracted from the first algae mat.

18. The method of claim 15, wherein the first algae mat is formed from the concentrated algae biomass of a *Chloralla* species and/or a *Spirulina* species, wherein the second saline water is treated with suitable levels of $CO_2$ and at least one of an acid and a base to grow the *Chloralla* species and/or the *Spirulina* species in the bioreactor, and wherein oil is extracted from the first algae mat.

* * * * *

UNITED STATES PATENT AND TRADEMARK OFFICE
CERTIFICATE OF CORRECTION

PATENT NO. : 10,113,213 B2
APPLICATION NO. : 15/264016
DATED : October 30, 2018
INVENTOR(S) : Khaled A. Abuhasel et al.

Page 1 of 1

It is certified that error appears in the above-identified patent and that said Letters Patent is hereby corrected as shown below:

On the Title Page

Item (71):
Please change "(71) Applicants: University of Bisha, Bisha (SA);
    Prince Sattam Bin Abdulaziz University, Alkharj (SA)"

To:
--Applicants: University of Bisha, Bisha, Saudi Arabia;
    Prince Sattam Bin Abdulaziz University, Alkharj, Saudi Arabia--.

Signed and Sealed this
Nineteenth Day of March, 2019

Andrei Iancu
*Director of the United States Patent and Trademark Office*